United States Patent [19]

Kawamura et al.

[11] Patent Number: 5,219,288
[45] Date of Patent: Jun. 15, 1993

[54] JAW BONE ANCHORED TYPE POSITIONER

[76] Inventors: Kunio Kawamura, 8-18 Umeda-cho, Moriyama-City, Shiga, Japan, 524; Kazuhiko Nagoshi, 39-D-506 Senriyamanishi 4-chome, Suita-City, Osaka, Japan, 565

[21] Appl. No.: 411,004

[22] Filed: Sep. 22, 1989

[30] Foreign Application Priority Data

Sep. 26, 1988 [JP] Japan .................. 63-241590

[51] Int. Cl.$^5$ .................................. A61C 19/04
[52] U.S. Cl. ......................... 433/229; 378/180
[58] Field of Search ............. 433/6, 68, 69, 229; 378/178, 180; 269/328

[56] References Cited

U.S. PATENT DOCUMENTS 2,032,833  3/1936  Broadbent ........................ 378/180
3,514,606  5/1970  Rabey ............................ 378/180

FOREIGN PATENT DOCUMENTS 0193650  9/1986  European Pat. Off. .
0301359  2/1989  European Pat. Off. .
7820937  7/1978  Fed. Rep. of Germany .
2499399  8/1982  France .
0643147  1/1979  U.S.S.R. ........................ 378/180

Primary Examiner—John J. Wilson
Attorney, Agent, or Firm—Cushman, Darby & Cushman

[57] ABSTRACT

A jaw bone anchored type head positioner for positioning the head of a subject which is employed in a cephalotomograph or temporomandibular joint radiograph using X rays or the like. A die patterned on an impression taken from the dentition of the subject is fixed to the positioner so that the head of the subject is fixed in position by means of the die.

3 Claims, 2 Drawing Sheets

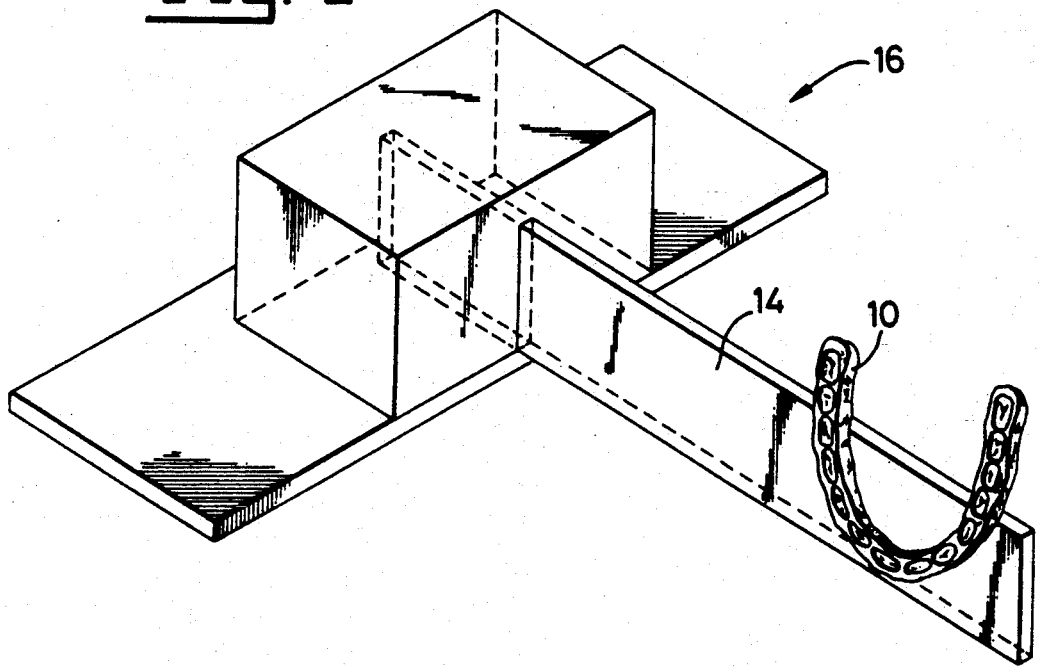
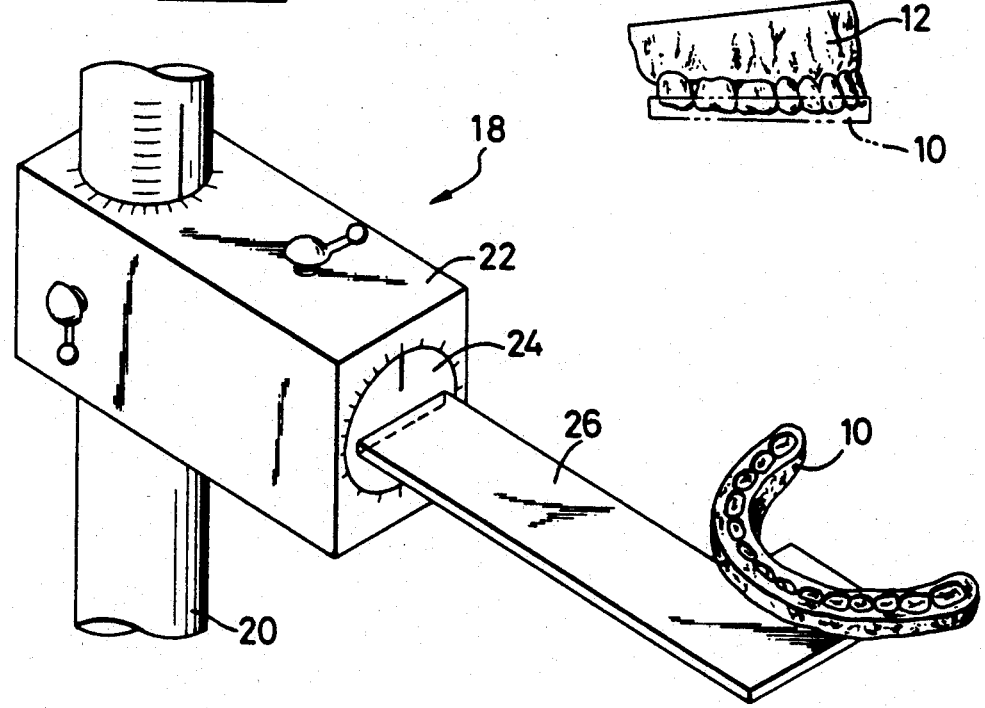

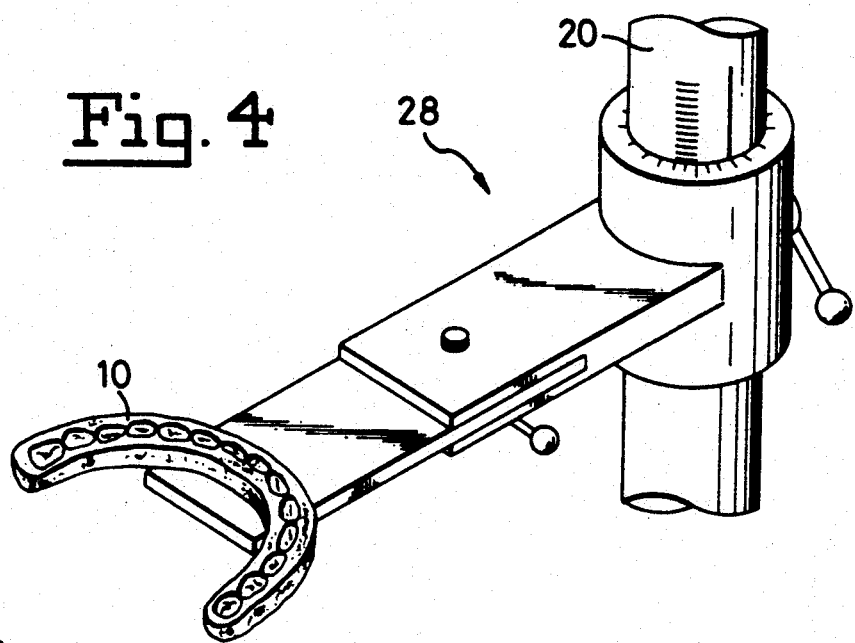
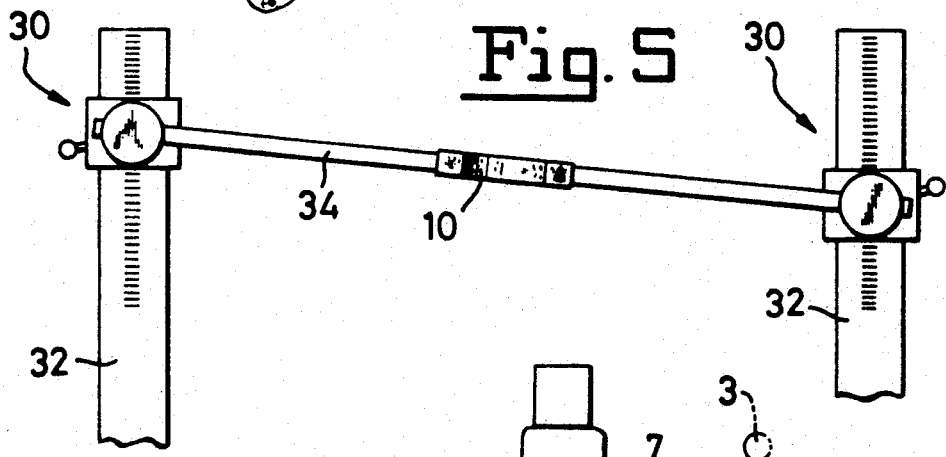
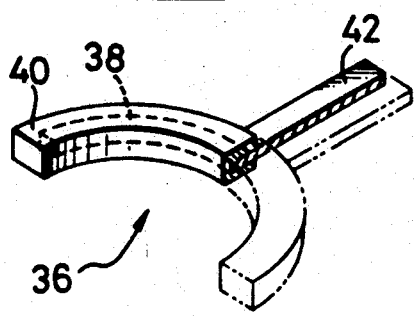
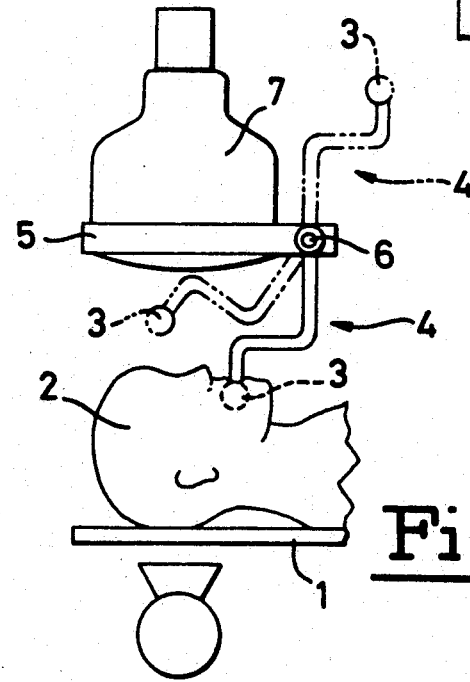

JAW BONE ANCHORED TYPE POSITIONER

BACKGROUND OF THE INVENTION

This invention relates to a head positioner for use in an X-ray or ultra-short wave cephalotomograph, computer tomograph, dental pantomograph, temporomandibular joint radiograph, and the like.

Hitherto, X-ray cephalotomography has been practiced mainly in neurosurgical diagnoses, while in dental diagnoses such photography has not been in general practice. Today, however, needs for radiotomography are increasing in dental fields such as oral surgery, temporomandibular joints, implantation, and orthodontic treatment, and it is desired that accurate and quantitative information be obtained repetitively in same conditions by radiotomography and otherwise on matters such as buccolingual denture inclination and antagonistic tipping angle; sectional configuration of jaw bones and, more particularly, cortical-bone configuration, spongy-bone distribution, and kinematic position of inferior alveolar veins; and spacial position of impacted third molar.

In this conjunction, various improvements have been made with respect to tomographic apparatuses per se, and tomographs which can exhibit good performance accuracy have been proposed. However, insofar as head positioners for use in radiotomography, no such positioner has been proposed which can exhibit good practical performance accuracy.

In Japanese Utility Model Laid-Open Publication No. 61-34209, for example, there is described a technique for fixing the head of a subject in position by means of an anchor band. In Japanese Patent Laid-Open Publication Nos. 61-94639, 60-58127, and 61-203948, there are disclosed techniques such that a fixing member is applied to the ears, cranial fossa, or the like portion of the subject to fix the head in position. However, these techniques are designed to fix the head of the subject through the intermediary of a skin portion or the hair of the subject over which the fixing member is applied, and therefore no satisfactory positioning can be achieved because of the resiliency of the skin or other portions; furthermore, the head cannot be tightly bound by the anchor band or fixing member, which in fact also prevents the head from being completely fixed in position. As such, with these head positioners, the head of the subject cannot be repeatedly fixed in same conditions and it is virtually impossible to obtain laminograms of the subject under same conditions during the pre-treatment, in-treatment, and post-treatment stages.

Japanese Utility Model Laid-Open Publication No. 61-14006 discloses a head positioner which can solve these problems to some extent. This head positioner, as FIG. 7 shows, comprises a fixing device 4 having a spherical element 3 adapted to be inserted in the palate of a subject 2 laid down on a bed 1 and to be subjected to a bite by the subject 2, the fixing device 4 being pivotally supported by a supporting member 5 of an image intensifier or the bed 1, and a mechanism 6 for fixing the fixing device 4 to a desired rotation angle position. However, since this positioner is such that the spherical element 3 of the fixing device 4 is inserted in the palate of the subject 2 and subjected to a bite, the positional relation between the spherical element 3 and the palate of the subject 2 is unstable; and therefore the positioner cannot be put in use unless the subject 2 is laid down on the bed. Another problem is that because of such instability, the relative position of the subject 2 and the image intensifier 7 cannot be constantly defined, which in fact means poor duplicability. Furthermore, the insertion of the spherical element is a possible cause of pain to the subject 2, and the positioner cannot be employed for purposes of jaw bone photographing.

BRIEF SUMMARY

The object of the invention is to provide a head positioner which permits repetitive reproduction of initially set head positioning conditions in the practice of cephalotomography and the like.

In accordance with the invention a jaw bone anchored type head positioner is provided which comprises:

(a) a die duplicated from an impression taken with respect to the whole or a part of the dentition, dentulous or edentulous, of one or both of the upper and lower jaws of a subject, (b) a supporting member formed integrally with or separately from said die for supporting said die, and (c) fixing means for controlling said die continuously or stepwise to a desired position through said supporting member and for removably fixing said supporting member in position, whereby when the subject is caused to have a bite of said die, the jaw bones of the subject can be anchored to the die and accordingly the head of the subject can be fixed in position.

Ear rods and a nasion support adjusted to the nose of the subject are supplementarily used in combination with the supporting member.

According to such arrangement of the invention, a die is duplicated from the dentition of one or both of the upper and lower jaws of the subject. When the jaw bone or bones are dentulous, the die is prepared with respect to the dentulous dentition, or if the jaw is toothless, in addition to a model obtained on the basis of an impression taken from the alveolar ridge, a base plate is prepared which, together with the model, is held in position by means of an edentulous jaw skater. An impression for die making may be taken with respect to the whole or a part of the dentition. The die duplicated on the basis of the impression taken from a subject has a support member formed integrally therewith or securely fixed thereto, by which the die is supported in position. The supporting member is fitted in a fixing device mounted in a tomograph or the like, in such a way that the die fixed to the supporting member is adjusted to be finally positioned and oriented properly in relation to the section to be tomographed.

The die fixed through the supporting member to the fixing device is subjected to biting by the subject, whereby the dentition and the die come into engagement with each other so that the jaws and head of the subject are fixed to the fixing device through the die.

BRIEF DESCRIPTION OF THE DRAWINGS

FIG. 1 is a perspective view showing one form of jaw bone anchored type head positioner embodying the invention;

FIG. 2 is a side view showing a plaster model of teeth for the preparation of a die for the head positioner in FIG. 1;

FIGS. 3, 4 and 5 are views showing other embodiments of the invention, FIGS. 3 and 4 being perspective views, FIG. 5 being a front view;

FIG. 6 is a perspective view, partly in section, showing a structure for the preparation of a die representing another embodiment of the invention; and FIG. 7 is a side view showing, by way of example, a conventional head positioner.

DETAILED DESCRIPTION OF THE INVENTION

One embodiment of the invention will now be described in detail with reference to the accompanying drawings.

In FIG. 1, the reference numeral 10 designates a die which, in the present embodiment, is patterned on an dentition impression taken from one of the upper and lower jaws of a subject. To produce die 10, a plaster model 12 as shown in FIG. 2 is first made by a certain technique conventionally employed in dental practice, and then a resin splint 10 removably attachable to the plaster model 10 is prepared. The die 10 is formed of a reaction setting resin or the like resin material which is less liable to volume shrinkage or expansion.

The site and direction of a particular section to be tomographed using the die 10 and plaster model 12 thus prepared are selected, and the die 10 is fixed to a resin-made supporting member 14 in a direction convenient for tomographing purposes. The direction in which the die 10 is fixed to the supporting member 14 may vary according to the type of the tomograph to be employed, and is suitably selected accordingly.

The supporting member 14 is mounted to a fixing device 16 placed on a table of the tomograph not shown and is clamped to position by a clamp not shown. The fixing device 16 is held constant in position relative to the tomograph so that the supporting member 14 fixed to the fixing device 16 is liable to no variation in position relative to the tomograph. Therefore, the die 10 which has been fixed to the supporting member 14 after having been suitably positioned and oriented in relation thereto is fixed in position as set relative to the tomograph.

When the die 10 thus fixed to the tomograph is placed between the jaws of the subject for being lightly bitten, the die 10 goes into close engagement with the dentition of the subject and accordingly the jaw bones of the subject are held stable, the head of the subject being thus steadily fixed to the tomograph through the fixing device 16. The supporting member 14 to which the die 10 is fixed may be repeatedly mounted to and dismounted from the fixing 16 without being liable to variations in setting position and direction with respect to the die 10. The dentition of the subject is unlikely to change over a considerably long period of time, if the subject is an adult, or of the subject is an infant, the dentition is subject to no or little change for a period of several to tens of months; therefore an initial die 10 may be repetitively used. In the case where some change has been caused to the dentition of the subject due to the application of an implant or otherwise, the die 10 may easily be restored to a usable condition by eliminating a part of the die 10 which corresponds to the site of such change in the dentition.

The die permits proper occlusion through close contact with the teeth of the subject can produce no backlash relative to the teeth. Except where unusual conditions are present, the die permits no jolting with respect to the dentition and jaw bones. By causing the subject to bite lightly the die, the jaw bones are positionally stabilized and thus the head of the subject can be steadily fixed to the fixing device.

In this way the jaw bones and joints can be accurately fixed in position simply by the subject being caused to bite the die to bring it into good occlusion relation with the teeth. Furthermore, both the jaw bones and the head can always be fixed in position under predetermined conditions during all relevant stages including pre-treatment, under-treatment, and post-treatment stages, and thus more accurate diagnosis and treatment can be given through comparative studies of laminograms obtained under predetermined conditions.

In the case where the die is fixed to the supporting member after being positionally adjusted to the latter so that the site and orientation of a particular section to be tomographed may readily be located, same conditions can be repetitively obtained simply by fixing the supporting member to the fixing device. In the case where the die is fixed to the supporting member constantly as preset with respect to the positional relationship between the former and latter, the supporting member is fixed to the fixing device through suitable adjustment made so as to provide the site and orientation of the particular section to be tomographed, and thus, any time thereafter, the supporting member can be fixed to the fixing device according to the adjustment data, whereby same conditions can be repetitively obtained for positional relationship between the die and the fixing device.

For the purpose of jaw joint radiographing at a desired site of the lower jaw, a fixation source is set on a molar tooth buccal surface of the upper jaw. For die mounting and dismounting, a movable clutch hinged at a median portion is prepared which is to be accurately fixed to the molar tooth buccal surface of the upper jaw. The hinge is graduated to provide reference for purposes of duplicativity acknowledgement.

One embodiment of the invention has been described above; however, the invention may be practiced in other forms.

As FIG. 3 shows, for example, a fixing device 18 comprises a guide rod 20 provided in a tomograph, a slidable-rotatable member 22 which is slidable along and rotatable about the guide rod 20, and a rotatable member 24 rotatably provided in the slidable-rotatable member 22, the guide rod 20, slidable-rotatable member 22, and rotatable member 24 being clamped by a clamp to position as set according to the scale on each of them. The rotatable member 24 of the fixing device 18 has an insertion hole bored therein for releasably receiving a supporting member 26 to which the die 10 is fixed. The supporting member 26 is inserted at one end into the insertion hole and fixed in position.

According to this embodiment, the die 10 can be fixed to the supporting member 26 as desired, and the orientation of the die 10, that is, the site and orientation of a particular section to be tomographed, is suitably determined by the fixing device 18. In this embodiment, by recording the graduation set on the fixing device it is possible to accurately duplicate the mounting position for the die 10. As a modified form of this embodiment, the guide rod 20 of the fixing device 18 may be adapted to be movable relative to the tomograph.

In another embodiment, as FIG. 4 shows, guide rod 20 of a fixing device 28 may be disposed in front of the subject. In this embodiment, as well as in FIG. 3 embodiment, various forms of fixing device may be employed according to the site and orientation of the section to be tomographed. It is desired that the arrangement of the fixing device be modified correspondingly to the type of the tomograph to be used, as well as various other kinds of apparatuses to be used, such as X-ray television fluoroscopic photograph and dental pantomograph; and the present invention can immediately meet such requirement.

In another embodiment, as FIG. 5 shows, a fixing device 30 has a pair of guide rods 32, and a supporting member 34 extending beteen the guide rods 32 and obliquely fixed thereto so as to determine the site and orientation of the section to be tomographed.

In the embodiments shown in FIGS. 3 to 5, the guide rod or rods of the fixing device may be disposed either vertically or horizontally so as to meet varying conditions such that photographing may be made with the subject as postured in sitting position or lying position according to the type of photographing apparatus used.

In the above described embodiments of the invention, the die 10 is based on a plaster model made according to the conventional dental technique. Such plaster model is made with respect to one of the upper and lower jaws of the subject that requires diagnosis and treatment in particular.

A die can not only be made on the basis of a plaster model, but also it may be constructed in such a way that, as FIG. 6 shows, for example, the die comprises a structure 36 having a core 38 centrally formed therein, the core 38 being covered all over with a resin material 40. In this embodiment, the resin material 40 is a thermosetting resin, for example, and the subject is caused to take a bite of the structure 36 formed of the thermosetting resin 40 so that a mark of upper and lower teeth is transferred onto the surface of the structure 36; thereafter, the structure 36 having the teeth marks is heat treated so as to allow the resin 40 to be hardened into a die. The resin 40 may be a thermosetting resin; and of course it is possible to construct a die of such resin.

In this embodiment, the core 38 of the structure 36 is formed integrally with a supporting member 42, whereby the trouble of fixing the supporting member 42 to the die 36 is saved. The core 38 prevents the structure 36 from being bitten off when the subject is caused to have a bite of the structure 36 to produce an impression of teeth thereon, and it is also effective as a reinforcement for the die 36 prepared. The core 38 may be provided only for a part of the structure 36.

Several embodiments of the invention have now been described. Not only can the apparatus of the invention be employed for purposes of dental diagnosis and treatment, but also it can be advantageously employed for cephalotomographic purposes in connection with neurosurgical diagnosis and therapy and otherwise, and more particularly in the case where laminograms in same conditions are repeatedly required at stages prior to during and after treatment. It is not intended that the invention is limited to the art of tomography; needless to say, the invention may be advantageously employed in other photographic areas.

When using the jaw bone anchored type head positioner according to the invention, an ear rod may be used in combination, or in place of or in conjunction with the ear rod, a nasion support adjusted to particular conditions of the subject may be supplementarily used in combination.

The die may be formed with respect to only a portion of the dentition. The fixing device may be adapted for fine adjustment by a toothed wheel or the like. Further, it is possible to arrange for enabling the supporting member to be not only continuously but also stepwise adjusted by the fixing device. It will be obvious to those skilled in the art, therefore, that many changes, modifications, and variations of the invention may be made without departing from the spirit and scope of the invention.

ADVANTAGES OF THE INVENTION

As above described, according to the invention, a die constructed so as to meet particular conditions of each individual subject is applied for fixing the jaw bones and joints, and head of the subject by causing the subject to have a bite of the die, so that those parts of the subject can be properly fixed in position without the possibility of becoming unstable.

The die is fixed to the fixing device through the supporting member; therefore, the jaw bones and joints, and the head can be repetitively accurately fixed in position under same conditions. Therefore, the positioner of the invention provides good duplicability, and yet it is comparatively simple in construction and economical.

Furthermore, the die is patterned on an impression of the dentition of the subject; and therefore, when the subject is caused to have a bite of the die for occlusion, no feeling of physical disorder can be caused to the subject, nor can any pain be caused.

What is claimed is:

1. A jaw bone anchored type positioner, comprising:
   a die duplicated from an impression taken with respect to at least a portion of one of the dentition, dentulous and edentulous of at least one of the upper and lower jaws of a subject, said die being formed by transferring a mark of at least a part of the dentition, dentulous or edentulous, of one of both of the upper and lower jaws of the subject;
   a supporting member, attached to said die for supporting said die;
   means for fixing said supporting member in a first predetermined position, relative to a fixed surface, whereby a head of said subject will be fixed in a second predetermined position solely by virtue of contact between said die and at least one of said upper and lower jaws of said subject; and
   means for reproducing said first predetermined position so as to allow the head of said subject to be subsequently fixed in said second predetermined position.

2. A jaw bone anchored type positioner, comprising:
   a die duplicated from an impression taken with respect to at least a portion of one of the dentition, dentulous and edentulous of at least one of the upper and lower jaws of a subject;
   a supporting member, attached to said die for supporting said die, said supporting member being formed separately from said die;
   means for fixing said supporting member in a first predetermined position, relative to a fixed surface, whereby a head of said subject will be fixed in a second predetermined position solely by virtue of contact between said die and at least one of said upper and lower jaws of said subject; and
   means for reproducing said first predetermined position so as to allow the head of said subject to be subsequently fixed in said second predetermined position.

3. A jaw bone anchored type positioner, comprising:

a die duplicated from an impression taken with respect to at least a portion of one of the dentition, dentulous and edentulous of at least one the upper and lower jaws of a subject;

a supporting member, attached to said die for supporting said die;

means for fixing said supporting member in a first predetermined position, relative to a fixed surface, whereby a head of said subject will be fixed in a second predetermined position solely by virtue of contact between said die and at least one of said upper and lower jaws of said subject, said fixing means controlling said die in a continuous manner; and means for reproducing said first predetermined position so as to allow the head of said subject to be subsequently fixed in said second predetermined position.

* * * * *